United States Patent
Konishi

(10) Patent No.: US 6,365,192 B1
(45) Date of Patent: Apr. 2, 2002

(54) BIOACTIVATING SUBSTANCE

(75) Inventor: Jin-emon Konishi, Osaka (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/551,135

(22) Filed: Apr. 17, 2000

(30) Foreign Application Priority Data

Apr. 15, 1999 (JP) .......................................... 11-108221

(51) Int. Cl.$^7$ ...................... A61K 35/12; A61K 31/395; A01N 63/00
(52) U.S. Cl. ...................... 424/520; 424/93.6; 424/665; 423/324; 423/326; 514/210
(58) Field of Search ............................. 424/93.6, 520, 424/665; 423/324, 326; 514/210

(56) References Cited

U.S. PATENT DOCUMENTS

| | | | |
|---|---|---|---|
| 4,089,883 A | 5/1978 | Blount | |
| 4,863,518 A | 9/1989 | Blount | |
| 4,985,254 A | 1/1991 | Konishi et al. | |
| 4,985,354 A | 1/1991 | Toyomaki et al. | |
| 5,013,558 A | 5/1991 | Konishi | |
| 5,057,324 A | 10/1991 | Shibayama et al. | |
| 5,534,509 A | 7/1996 | Konishi et al. | |
| 5,560,935 A | 10/1996 | Konishi et al. | |
| 5,658,896 A | 8/1997 | Konishi et al. | |
| 5,807,951 A | 9/1998 | Konishi et al. | |
| 6,051,613 A | 4/2000 | Ohno et al. | |
| 6,165,515 A | * 12/2000 | Matsuyama et al. | ........ 424/520 |

FOREIGN PATENT DOCUMENTS

| | | |
|---|---|---|
| EP | 0 300 973 | 1/1989 |
| EP | 0 315 591 | 5/1989 |
| EP | 0341209 A2 | 11/1989 |
| EP | 0 348 353 A2 | 12/1989 |
| EP | 0 621 038 A1 | 10/1994 |
| EP | 0 645 142 A1 | 3/1995 |
| EP | 0 953 352 A1 | 11/1999 |
| GB | 697351 | 9/1953 |
| JP | 53-101515 | 9/1978 |
| JP | 57-77697 | 5/1982 |
| JP | 58-035117 | 3/1983 |
| JP | 63/025600 | 5/1988 |
| JP | 63/039572 B | 8/1988 |
| JP | 03/043279 | 7/1991 |
| JP | 2594222 | 12/1996 |
| WO | WO 93/08828 | 5/1993 |

OTHER PUBLICATIONS

Takeoka, Y. et al., "Influence of Neurotropin on Thymic Microenviromental Abnormalities of NZB Mice," *Int. J. Immunotherapy*, XI(2), pp. 49–56 (1995).
"Drugs in Japan, Ethical Drugs," Yakugyo Jiho Co., Ltd., 1994, p. 1434–1435.
Yokoi et al., "Effect of Degree of Polymerization of Silicic Acid on the Gastrointestinal Absorption of Silicate in Rats," *Chem. Pharm. Bull.*, vol. 27, No. 8, 1979, pp. 1733–1739.
Derwent Publications Ltd., London, GB: AN 82–10241J, "Drug For Cultivated Fish," & JP A57183720 (Mitani J.), Nov. 12, 1982, abstract.
"Remedy For Burn," *Patent Abstracts of Japan*, vol. 7, No. 255 (C–189), Oct. 6, 1983, & JPA58121217 (Kagitani Takeo) Jul. 19, 1983, abstract.
"Drug for Food Poisoning," *Patent Abstracts of Japan*, vol. 11, No. 371 (C–462), Dec. 3, 1987 & JPA62145022 (Sofuto Shirika) Jun. 29, 1987, abstract.
"Adsorbent For Peroxylipid," *Patent Abstracts of Japan*, vol. 15, No. 474 (C–890), Dec. 3, 1991 & JPA3204803 (Shiscido Co., Ltd.) Sep. 6, 1991, abstract.
The Merck Index, 9th ed. 1976, No. 7456, 8443, 8233–8243 & 5514–5515.
Section CH, Week 9645, Derwent Publications Ltd., Class B04, AN 96–450925 XP002109698 & JP 08 225452 A, Sep. 3, 1996, abstract.
De Reuck J., et al., "A double–blind study of neurotropin in patients with acute ischemic stroke,", *ACTA Neurologica Scandinavia* vol. 89, No. 5, 1994, pp. 329–335, XP002109696.
Sprumont, et al., "Morphometrical Quantification of Brain Edema Related to Experimental Multiple Micro–Infarcts in Mice: Assessment of Neurotropin Effect," *Meth Find Exp Clin Pharmacol* 1993, 15(3): 169–177, XP002109697.
Database BIOSIS, XP–002113089, Li S–Y, et al. Studies on the Protective Action of Silicon Compound of Equisetum Against Experimental Liver Injury in Rats and Mice & Zhongguo Yaolixue Yu Dulixue Zazhi. ISSN: 1000–3002, abstract.

* cited by examiner

Primary Examiner—Christopher R. Tate
(74) Attorney, Agent, or Firm—Hollander Law Firm, P.L.C.

(57) ABSTRACT

A highly active bioactivating substance which exhibits suppressing action on histamine liberation and inhibition of hyaluronidase activity may be obtained by adding a silicate to an extracted substance from tissues activated by adding internal or external stressors to animals or animal tissues such as infecting with poxvirus. The highly active bioactivating substance may also be obtained by performing a special extraction to effect a high content of silicic acid in the extracted substance from the activated tissues. The bioactivating substance may be in the form of a powder and may have a silicon component content which is more than 20 $\mu$g, for example greater 22 $\mu$g, preferably greater than 25 $\mu$g, calculated as silicon per mg of dried substance. The powder may be obtained by admixing an extract from activated tissue, which extract contains at least one silicon component, with at least one additional silicon component to obtain a mixture, and drying the mixture to obtain a powder which exhibits positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), and negative qualitative reactions to protein (by a trichloroacetic acid method) and phenol (by a ferric chloride method).

20 Claims, No Drawings

BIOACTIVATING SUBSTANCE

FIELD OF THE INVENTION

The present invention relates to a highly active bioactivating substance having a high silicon component content. The bioactivating substance may be obtained by adding a silicate to an extracted substance from tissues activated by adding internal or external stressors to animals or animal tissues, or by carrying out a special extraction to make the content of silicic acid high in the extracted substance from the activated tissues.

BACKGROUND OF THE INVENTION

Living organisms survive as an individual by adjusting and maintaining their physical and chemical states to and within certain stable physiological conditions by adapting to the changes in internal and external circumstances. To maintain such homeostasis, the living organism always produces various substances in vivo. Upon invasion by viruses or bacteria, and upon generation of tumor cells, it also produces resistant substances in vivo to such external and internal invasions.

However, when the biofunctional balance is disturbed and the unbalanced state becomes chronic, various diseases result. The ideal way of curing the disease is to recover from the abnormal state of the unbalanced biofunction to a normal state by invigorating and regulating homeostasis of the living body. It is well known that various receptors and ion channels such as sodium, potassium and calcium channels on cell surfaces especially carry out the maintenance and normalization of biofinctions. It is also known that, upon growing older, the ability of DNA to recover against damage decreases in mammalian cells and that the production of free radicals in vivo promotes aging and the generation of collagen disease and cancer. Collagen is a noncellular substance widely present in skin, blood vessels, cartilage, eyeballs and kidneys. A crosslinking of collageneous materials proceeds with aging and their elasticity decreases and they become hard.

Histamine is released from mast cells upon the antigen-antibody reaction and causes various allergic reactions. A suppressive ability for mast cell degranulation may contribute to normalization of the abnormal diseased state.

The present inventor has focused on the homeostatic functions of a living body, which regulate and restore the neurological, immunological and endocrinological disturbances due to functional abnormality in the diseased state. He has conducted an extensive investigation to ascertain resistant substances produced in vivo to external and internal stresses. As a result of such investigations on substances produced from activating living tissues, which enhance the natural curing activity and normalize the functions of a living body, the present inventor has found a highly active bioactivating substance and accomplished the present invention.

In the present invention, a high silicon component content, bioactivating substance is obtained from an extract from activated or stressed tissues and a silicate. The bioactivating substance of the invention is a biofunction-regulating and maintaining substance which may cure and normalize the abnormal functions occurring in a diseased state. It exhibits physiological activities such as unexpectedly superior suppressing action on histamine liberation and inhibition of hyaluronidase activity. It may be employed in pharmaceutically effective amounts in pharmaceutical compositions for the treatment of allergies in patients known to be in need of such treatment.

SUMMARY OF THE INVENTION

The present invention provides a highly active bioactivating substance comprising an extract from activated tissue. The bioactivating substance has a silicon component content of greater than 20 $\mu$g, for example greater than 22 $\mu$g, preferably greater than 25 $\mu$g, which is calculated as silicon per mg of dried substance. To obtain the bioactivating substance of the present invention, various animals or animal tissues are inoculated with viruses or tumor cells as a stressor to activate the tissues, a physiologically active substance is extracted from the activated tissue and a soluble silicate is added thereto, The bioactivating substance of the present invention may also be prepared by a special extracting method to obtain a high content of silicic acid in the extracted substance from the activated tissue. In embodiments of the present invention, the ratio of the silicon component content of the extract from the activated tissue calculated as silicon to the total silicon component content of the bioactivating substance calculated as silicon is 1:3 to 1:10. The bioactivating substance of this invention exhibits physiological activities such as unexpectedly high suppressing action on histamine liberation and inhibition of hyaluronidase activity. The bioactivating substance of the invention is a biofunction-regulating and maintaining substance which may cure and normalize abnormal functions occurring in a diseased state.

DETAILED DESCRIPTION OF THE INVENTION

The present invention provides a bioactivating substance which suppresses histamine liberation from mast cells and inhibits hyaluronidase activity comprising an extract from activated tissue. The extract and the bioactivating substance containing it comprise at least one silicon component. In embodiments of the invention, at least one additional silicon component is admixed with the extract from activated tissue to obtain a mixture, and the mixture is dried to obtain a powder form of the bioactivating substance of the present invention. The bioactivating substance of the present invention, and the dried extract from the activated tissues, exhibit positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), and negative qualitative reactions to protein (by a trichloroacetic acid method) and phenol (by a ferric chloride method). The bioactivating substance of the present invention obtained by admixing the extract from the activated tissue and the additional silicon component, has a silicon component content which is more than 20 $\mu$g calculated as silicon per mg of dried substance. The additional silicon component substantially increases the silicon component content of the extract from activated tissues and substantially increases its physiological activity. In embodiments of the present invention, the bioactivating substance may have a silicon component content of greater than 22 $\mu$g, preferably greater than 25 $\mu$g, which is calculated as silicon per mg of dried substance. The ratio of the silicon component content of the extract from the activated tissue calculated as silicon to the total silicon component content of the bioactivating substance calculated as silicon may be 1:3 to 1:10. The total silicon component content of the bioactivating substance includes silicon components naturally or originally present in the extract from activated animal tissues and any silicon components contributed by admixing the extract with additional silicon components not naturally or originally present in the extract from activated animal tissues.

The bioactivating substance may be obtained by activating or stressing animal tissue, grinding the activated animal tissues, adding a solvent for extraction to the ground tissue, removing the tissue pieces, removing protein from the remaining mixture, adsorbing the residue with an adsorbent, eluting the adsorbed components from the adsorbent, and then adding a predetermined amount of a soluble silicate to the resulting physiologically active substance as extracted above. The bioactivating substance of the present invention can also be obtained by a special extracting method,.i.e., all eluting operation from the adsorbent is carried out to make the content of silicic acid high.

In embodiments of the invention, extracts from an activated tissue which may be employed in the compositions and methods of the present invention may be extracts from inflammatory tissue inoculated with vaccinia virus disclosed in Japanese Examined Patent Publications Sho-631039,572 B, Sho-63/025,600 B and Hei-03/043,279 B, Japanese Patent No. 2,594,222 and U.S. Pat. No. 5,013,558 to Konishi and 5,560,935 to Konishi, et al. The disclosures of Japanese Examined Patent Publications Sho-63/039,572 B, Sho-63/025,600 B and Hei-03/043,279 B, Japanese Patent No. 2,594,222, and U.S. Pat. No. 5,013,558 to Konishi and U.S. Pat. No. 5,560,935 to Konishi, et al. are herein incorporated by reference in their entireties. A method for producing an extract from inflammatory tissue inoculated with vaccinia virus for use in the present invention is described, for example, in Example 1 of Japanese Examined Patent Publication Sho-63/039,572 B and Japanese Patent No. 2,594,222. Methods for producing extracts from inflammatory tissue inoculated with vaccinia virus for use in the present invention are also described, for example, in U.S. Pat. No. 5,013,558 to Konishi at column 1 line 44 to column 3 line 22, and in Examples 1 and 2 at column 3 lines 33 to 62, U.S. Pat. No. 5,560,935 to Konishi, et al. at column 2 line 55 to column 3 line 14, and column 3 line 33 to column 4 line 64, and in Examples 1 and 2 at column 5 line 6 to column 6 line 8, which are herein incorporated by reference in their entireties.

A commercially available drug preparation of an extract from inflammatory rabbit skin inoculated with vaccinia virus is sold in Japan under the trade name Neurotropin by Nippon Zoki Pharmaceutical Co., Osaka, Japan. As mentioned at pages 1,927 and 1,928 of "Drugs in Japan, Ethical Drugs" ($22^{nd}$ edition, 1998–1999; edited by Japan Pharmaceutical Information Center; published by Yakugyo Jiho Co., Ltd.), this preparation is a drug containing non-proteinous active substances extracted and isolated from inflammatory rabbit skin inoculated with vaccinia virus. The preparation has been used for treatment of lower back pain, neck-shoulder-arm syndrome, periarthritis scapulohumeralis, arthrosis deformans, symptomatic neuralgia, post-herpetic neuralgia, pruritis due to dermatological diseases (such as eczema, dermatitis and urticaria), allergic rhinitis, and sequelae of subacute myelo-optico-neuropathy (such as coldness, pain and paresthesia/dysesthesia). It is available as an ethical drug in the form of injections (subcutaneous, intramuscular and intravenous) and tablets.

Neurotropin was used in an experimental study at the School of Medicine, University of California, Davis, to evaluate its influence on thymic microenvironmental abnormalities of New England black mice as reported by Y. Takeoka et al, *Int. J Immunotherapy*, XI(2), pp. 49–56 (1995). As taught by Takeoka et al, Neurotropin is a nonprotein extract isolated from the inflamed dermis of rabbits inoculated with vaccinia virus and it has been reported in the literature as: 1) having beneficial effects on immune-depressed animals, 2) clinically useful as an analgesic and as an anti-allergy drug with few side-effects in humans, 3) improving the immune status of murine lupus in (NZB/NZW) F1 mice, and 4) inhibiting the development of EAE in Lewis rats, an autoimmune model of human multiple sclerosis.

The commercially available extract, Neurotropin, may be used in the compositions and methods of the present invention. The descriptions, properties and dosages of Neurotropin reported in the above-mentioned "Drugs in Japan, Ethical Drugs" and the Takeoka et al article are incorporated herein by reference in their entireties.

The animal tissues used in the present invention are cultured tissues, cultured cells or inflammatory tissues of human or animal origin which are infected with virus, or chorio-allantoic membranes of embryonated eggs infected with virus. Examples of the virus used for the activation of the animal tissues as a stressor are orthopox viruses such as vaccinia virus, cowpox virus, variola virus, ectromelia virus and simian pox virus, parapoxviruses such as Orf virus, paravaccinia virus and bovine nopplelike stomatitis virus, goatpox viruses such as sheep pox virus, goatpox virus and lumpy skin disease virus, avian pox viruses such as avian pox virus and hare fibroma virus, rabbit pox viruses such as rabbit myxoma virus and rabbit fibroma virus, swine pox virus, Yava monkey tumor virus, Tara pox virus and other viruses belonging to the poxvirus family. As to tumor cells which may be used as a stressor, various tumor-cultured cell strains derived from human beings and animals may be used and anything that can be inoculated into the above animals and animal tissues to cause stress or activation can be employed. Mixtures of different strains of tumor cells can be inoculated into the animals and animal tissues to cause stress or activation. Also, the stressors may include combinations of viruses and tumor cells.

Exemplary of animals which may be used for preparing the activated tissues are domestic animals and fowl such as rabbits, cows, horses, sheep, goat, swine and chickens, and mammals such as monkeys, rats, mice, guinea pigs and hamsters. They may be selected depending upon the type of the stressors and the object or pharmaceutical effect desired. Regarding the cultured cells, any cell will do provided the stressor used is able to grow there. Examples of such cells which may be utilized for the culture are various tissues (e.g. human hemocytes and placentae) and the cultured cells of various tissues such as kidney, skin, lung, testis, lung, muscle, adrenal gland, thyroid gland, brain, nerve cells and hemocytes of the above-mentioned animals and embryos thereof.

The activated tissues or cells are aseptically collected, ground and made into an emulsified suspension by adding 1 to 5 times as much extracting solvent thereto. Examples of the extracting solvent applicable are distilled water, physiologically saline solution, weakly acidic or weakly basic buffers, etc. If necessary, stabilizers such as glycerol, antibacterial/antiseptic agents such as phenol, inorganic salts such as sodium chloride, potassium chloride and magnesium chloride may be added thereto in conventional amounts. At that time, the extraction can be facilitated by subjecting the admixture to treatment by means of freezing/melting, ultrasonic wave, cell membrane dissolving enzymes or surface-active agents.

The resulting milky extract is filtered or centrifuged to remove the tissue residue and then proteins are removed therefrom. Removal of the proteins can be carried out by known methods and treatments such as heating, ultrasonic waves, protein denaturing agents such as acids, bases, urea, guanidine, organic solvents and surface-active agents, isoelectric precipitation, salting-out, and the like. Then the proteins separated out therefrom are filtered off by means of filtration using filter paper (cellulose, nitrocellulose, etc.), a glass filter, Celite or a Seitz filter as well as ultrafiltration, gel filtration, an ion exchange resin, centrifugation and the like.

The resulting extracted fraction is adjusted to an acidic pH, preferably to pH 3.5–5.5, by an acid such as hydrochloric acid, sulfuric acid or hydrobromic acid, and adsorbed with an adsorbent. Examples of adsorbents which may be used are activated charcoal, kaolin and ion exchange resins. The adsorbent may be added to the extract followed by stirring or the extract may be passed through a column filled with the adsorbent whereby the effective component can be adsorbed.

In eluting the physiologically active substance of the present invention from the adsorbent, an extracting solvent (e.g. a basic aqueous solution, a solution in a water-miscible solvent such as alcohol or a mixed solution thereof) may be added. The mixture is preferably adjusted to pH 9–12, and then the physiologically active substance is eluted at room temperature or by heating appropriately or with stirring. The absorbent is removed by a conventional manner such as filtration to complete the elution. Then, if necessary, means such as chromatography, ultrafiltration and dialysis using a reverse osmosis filtration or removal of the salt therefrom may be applied whereupon the physiologically active substance can be prepared in a more purified state. The resulting physiologically active substance extracted from the activated animal tissues as above contains silicon components in an amount of 1–20 $\mu$g which are calculated as silicon per mg of dried substance.

The silicon substances which are added to the above physiologically active substance to prepare the bioactivating substance of the present invention are water-soluble silicic acids, water-soluble silicates, polymers of water-soluble silicic acids, polymers of water-soluble silicates, or mixtures thereof. For example, the silicon components may each be added in its own form or a polymerized form of silicic acid such as orthosilicic acid, metasilicic acid, mesodisilicic acid, mesotrisilicic acid and mesotetrasilicic acid and salts thereof with an alkali or alkaline metal such as sodium and potassium or water glass. It is also possible to add light and heavy anhydrous silicic acid in a fused state in an alkaline solution. A substance prepared by an alkali fusion of minerals containing a high content of silicon such as crystal, quartz, feldspar, granite and periodotite can be added. A substance prepared by treating diatomaceous earth, bentonite glass or active carbon with an alkaline substance can also be employed. It is possible to add a soluble silicate extracted from a plant, animal or diatomaceous earth containing a high content of silicon, for example, scouring rush, murasaki reishi (a kind of bracket fungus of the genus Fomes), tochu (bark of Eucommia ulmoides), rice plant, barley, bamboo, susuki (Japanese pampas grass), field horsetail, sponge and diatom.

Silicate polymers which may be employed in the present invention for admixture with the extracts of the present invention may be silicate polymers disclosed in U.S. Pat. No. 5,534,509 to Konishi et al. The disclosure of U.S. Pat. No. 5,534,509 is herein incorporated by reference in its entirety.

It is further possible that, in the manufacture of the physiologically active substance from the activated tissues eluted from an adsorbent such as active carbon, kaolin and bentonite, the pH is raised, the elution time is extended or the elution temperature is raised. According to the elution operation, extra silicon substances from the adsorbent are mixed therewith to prepare the bioactivating substance of the present invention containing a high amount of silicic acid.

The silicon compound may be appropriately added to the extracted substance from the activated tissues depending upon the object for use or within such an extent that the function is not deteriorated. The silicon components contained in the substance of the present invention are water-soluble silicic acid or its polymer where silicates are polymerized. They may be present in a single or polymerized form of silicic acid such as orthosilicic acid, metasilicic acid, mesodisilicic acid, mesotrisilicic acid and mesotetrasilicic acid and salts thereof with an alkali or alkaline metal such as sodium and potassium. The bioactivating substance of the present invention contains such silicon substances in an amount of more than 20 $\mu$g, for example more than 22 $\mu$g, preferably more than 25 $\mu$g, which are calculated as silicon per mg of dried substance.

Preferred embodiments of the present invention are:

(1) A bioactivating substance which is extracted and manufactured from activated tissues, shows positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), shows negative qualitative reactions to protein (by a trichloroacetic acid method) and phenol (by a ferric chloride method) and contains silicon components in an amount of more than 20 $\mu$g which are calculated as silicon per mg of dried substance.

(2) The bioactivating substance according to the above paragraph (1), wherein silicate is added to the substance extracted from the activated tissues.

(3) The bioactivating substance according to the above paragraph (1), wherein silicate polymer is added to the substance extracted from the activated tissues.

(4) The bioactivating substance according to the above paragraph (1), wherein silicate prepared by dissolving silicon oxide with sodium hydroxide or potassium hydroxide is added to the substance extracted from the activated tissues.

(5) The bioactivating substance according to the above paragraph (1), wherein a soluble silicate extracted from plant, animal or diatomaceous earth containing a high content of silicon such as scouring rush, murasaki reishi (a kind of bracket fungus of the genus Fomes), tochu (bark of *Eucommia ulmoides*), rice plant, barley, bamboo, susuki (Japanese pampas grass), field horsetail, sponge and diatom is added to the substance extracted from the activated tissues.

(6) The bioactivating substance according to the above paragraph (1), wherein silicic acid prepared by the extraction of minerals containing a high content of silicon (such as crystal, quartz, feldspar, granite, periodotite and glass) with an alkali is added to the substance extracted from the activated tissues.

(7) The bioactivating substance according to the above paragraph (1), wherein the said bioactivating substance is obtained by increasing the addition of silicon in the eluting operation from the adsorbent during the extraction from the activated tissues.

The following non-limiting examples illustrate methods for the manufacture of the product of the present invention and physiological effectiveness of the product wherein all parts, percentages and ratios are by weight, all temperatures are in ° C., and all reactions are conducted at about atmospheric pressure unless indicated to the contrary:

EXAMPLE 1

Skin of a healthy adult rabbit was inoculated with vaccinia virus to activate or stress the tissues. The activated skin was aseptically removed, finely cut, water was added thereto and the mixture was ground using a homogenizer to prepare an emulsion. The emulsion was filtered with pressure, and then the resulting filtrate was adjusted to pH 5.0 with hydrochloric acid and heated at 100° C. with a steam flow. Proteins were removed by filtration, the filtrate was adjusted to pH 9.1 with sodium hydroxide, heated at 100° C. and filtered. The filtrate was adjusted to pH 4.1 and 2% of activated charcoal was added thereto. The mixture was stirred for two hours and was filtered. To the filtrate was added 5.5% of activated charcoal, and the mixture was stirred for two hours and filtered. The activated charcoal which was obtained for the first time at the filtration was mixed with water, adjusted to pH 9.9 with sodium hydroxide, stirred at 60° C. for 1.5 hours and filtered. Water was added to the first batch of activated charcoal and to the second batch of activated charcoal. The pH of each batch was adjusted to pH 10.9 with sodium hydroxide, stirred at 60° C. for 1.5 hours and filtered. The resulting filtrates were combined, neutralized with hydrochloric acid and dried in vacuo. The yield from 1 kg of the activated skin was 4 g. The physiologically active substance, i.e., the extract from inflamed skins inoculated with vaccinia virus, prepared as above exhibited the following properties:

(1) Characteristic: an amorphous and hygroscopic powder with pale yellowish brown color;
(2) Solubility: it is soluble in water, methanol and ethanol and is insoluble in benzene and ether;
(3) pH: 7.5;
(4) Ultraviolet absorptions: max=270 nm;
(5) Color reactions: amino acid (positive to a ninhydrin reaction), saccharide (positive to an orcinol-iron(III) chloride-hydrochloric acid method), phosphorus (positive to a molybdenum blue method), protein (negative to a trichloroacetic acid method) and phenol (negative to a ferric chloride method).

To 100 mL of water were added 1 g of the said extract from inflamed skins inoculated with vaccinia virus and 500 mg of sodium metasilicate (50 mg calculated as silicon). The solution was adjusted to pH 7.5 with hydrochloric acid and then evaporated to dryness in vacuo to give the bioactivating substance of the present invention in the form of a powder.

EXAMPLE 2

Light anhydrous silicic acid (3 g) and 2 g of sodium hydroxide were placed in a crucible made of platinum or nickel and stirred after addition of 13 ml of water thereto. This crucible was further heated to boil for 5 minutes and water was added thereto to make 100 mL. Silicon was contained in an amount of 1.4 g in 100 mL of this solution and the said solution was used as a silicic acid solution. To 100 mL of water were added 0.5 g of the extract of Example 1 and 2.1 mL of the silicic acid solution. The mixture was adjusted to pH 7.5 and then evaporated to dryness in vacuo.

EXAMPLE 3

The bioactivating substance of the present invention contains a high amount of silicon compounds as compared with known extracts from inflamed skins inoculated with vaccinia virus. The physiological activities of the bioactivating substance of the present invention are a suppressive action on histamine liberation from mast cells, an inhibitory action to hyaluronidase activity, a suppressive action on intranasal vascular permeability, a suppressive effect on allergic reaction of type II, and the like. In this example, suppressive action on histamine liberation from mast cells and inhibitory action to hyaluronidase are demonstrated and described in detail;

(1) Suppressive Action on Histamine Liberation from Mast Cells

Wister strain rats were decapitated and mast cells were isolated from abdominal cavities by a conventional method. To the cell solution were added a sample solution and compound 48/80, the mixture was allowed to stand at 37° C. for 10 minutes and cooled with ice to stop the reaction. The liberated histamine was determined by means of generation of fluorescence using o-phthalaldehyde. The suppressing rate to histamine liberation by addition of the tested sample was expressed in terms of %. Concentration of the extract from inflamed skins inoculated with vaccinia virus in the tested sample solution was adjusted to 15 mg/mL. Various amounts of the silicon compounds were added thereto to prepare the bioactivating substance of the present invention to be tested. The suppressing action to histamine liberation was tested in the samples wherein various concentrations of silicon substances were contained. As a result, it has been confirmed that the bioactivating substance of the present invention has a high activity. An example of the results is shown in Table 1:

TABLE 1

| HISTAMINE SUPPRESSION | |
| --- | --- |
| Silicon concentration in tested sample | Suppressing rate to histamine liberation |
| 100 µg/mL | 16.9% |
| 300 µg/mL | 43.4% |
| 400 µg/mL | 53.0% |
| 500 µg/mL | 65.1% |

(2) Inhibitory Action to Hyaluronidase Activity

In the inflammation reaction site of a PCA which is an allergic reaction, hyaluronidase activity increases accompanied with an acceleration of vascular permeability. It has also been reported that inhibition of hyaluronidase suppresses capillary permeability. In view of the above, a test for the inhibition of hyaluronidase activity was carried out using the bioactivating substance of the present invention.

Thus, 0.5 mL of a hyaluronidase standard solution (final concentration: 5 units/ml) and 0.5 mL of the sample solution were incubated at 37° C. for 10 minutes, an aliquot of 0.1 mL thereof was added to 0.9 mL of a hyaluronic acid solution (150 µg/ml) and the mixture was incubated at 37° C. for 15 minutes. The reaction was stopped by adding 5 mL of acetate buffer (pH 4.0) containing 2.5 mg of bovine serum albumin and, after five minutes precisely, absorbance at 540 nm was measured. An inhibiting rate for enzymatic activity was determined in comparison with a control which is an absorbance for a physiological saline solution used instead of the sample solution. Concentration of the extract from inflamed skins inoculated with vaccinia virus in the tested sample solution was adjusted to 15 mg/mL with various concentrations of the silicon components. The inhibiting action of the bioactivating substance of the present invention to hyaluronidase activity was tested. An example of the results is shown in Table 2:

TABLE 2

INHIBITION OF HYALURONIDASE

| Tested substance | Silicon concentration in tested sample | Inhibition rate |
|---|---|---|
| Extract from inflamed skins inoculated with vaccinia virus | 50 µg/mL | 10.9% |
| Bioactivating substance of the present invention | 500 µg/mL | 89.1% |

It is apparent from the results of the above-mentioned pharnacological tests that the bioactivating substance of the present invention exhibits unexpectedly high activity as compared with the known physiologically active substance extracted from activated tissues. The bioactivating substance of the present invention, therefore, is highly useful as a pharmaceutical agent such as an anti-allergic drug. The extract may be administered to patients known to be in need of treatment in pharmaceutically effective amounts so as to substantially suppress histamine and/or to substantially suppress hyaluronidase to a desired level.

The bioactivating substance of the present invention can be made into various pharmaceutical preparations by combining the substance with various pharmaceutical carriers or diluents by conventional means to obtain solid, semisolid, liquid or aerosol preparations for oral or parenteral use. In the formulation, the substance of the present invention may be used solely or together in pharmaceutically effective amounts with pharmaceutically effective amounts of other pharmaceutically active components for treating animals or humans.

In the case of injections, a solution or a suspension comprising the substance of the invention may be prepared using an aqueous or nonaqueous solvent such as distilled water for injections, physiologically saline solution, Ringer's solution, plant oil, synthetic fatty acid glycerides, higher fatty acid esters or propylene glycol, followed by adjusting the pH and isotonic condition. Further, the substance of the invention may be prepared as an injectable preparation which is dissolved upon actual use. Such agent may be prepared by freeze-drying with additives such as sodium chloride, lactose and mannitol.

In the case of preparations for oral administration, the substance of the invention per se or a mixture of it with suitable additives such as fillers (e.g. lactose, mannitol, corn starch and crystalline cellulose) may be combined together with: 1) one or more binders such as gum arabicum, corn starch and gelatin, 2) one or more disintegrating agents such as corn starch, potato starch, carmerose and carmerose calcium, 3) one or more lubricants such as talc and magnesium stearate, and (4) other pharmaceutically acceptable excipients including pharmaceutically acceptable bulking agents, moisturizers, buffers, preservatives, perfumes and the like to give tablets, diluted powders, granules or capsules.

Further, depending upon the state of the patient or the type of the disease, the substance may be made into other preparations suitable for the therapy. For example, the substance of this invention may be formulated into creams or ointments together with higher fatty acid esters, higher alcohols, propylene glycol, silicone oil, liquid paraffin, VASELINE or various surface-active agents, or into other formulations such as suppositories, inhalating agents, aerosols, cataplasms and eye drops.

The preferred dosage of the substance of the present invention may vary depending upon the type of the disease, the condition of the patient, age or sex of the patient, form of the preparation, method for the administration, term for the administration, etc. To achieve a desired effect, about 0.5 mg to about 200 mg per day, preferably about 1 mg to about 150 mg per day may be usually given to common adults by the oral route, although the present invention is not particularly limited to such dosage. In the case of a parenteral administration such as by injection, the preferred dosage, may be from ⅓ to ⅟₁₀ of the above-mentioned oral dosages because of the effects of absorption, etc. in the oral route.

I claim:

1. A bioactivating composition which suppresses histamine liberation and inhibits hyaluronidase activity comprising an effective amount of an extract obtained from activated animal tissue infected with a poxvirus, wherein said bioactivating composition comprises at least one silicon component and exhibits positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), and negative qualitative reactions to protein (by a trichloroacetic acid method) and phenol (by a ferric chloride method), said bioactivating composition having a silicon component content which is more than 20 µg calculated as silicon per mg of dried composition.

2. A bioactivating composition as claimed in claim 1 wherein at least one silicate is admixed with the extract from the activated tissue.

3. A bioactivating composition as claimed in claim 1 wherein a silicate polymer is admixed with the extract from the activated tissue.

4. A bioactivating composition as claimed in claim 1 wherein a silicate prepared by dissolving silicon oxide with sodium hydroxide or potassium hydroxide is admixed with the extract from the activated tissue.

5. A bioactivating composition as claimed in claim 1 wherein a soluble silicate extracted from plant, animal or diatomaceous earth is admixed with the extract from the activated tissue.

6. A bioactivating composition as claimed in claim 5 wherein said added soluble silicate is extracted from scouring rush, murasaki reishi (a bracket fungus of the genus Fomes), tochu (bark of *Eucommia ulmoides*), rice plant, barley, bamboo, susuki (Japanese pampas grass), field horsetail, sponge, or diatom.

7. A bioactivating composition as claimed in claim 1 wherein silicic acid prepared by extraction of minerals with an alkali is admixed with the extract from the activated tissue.

8. A bioactivating composition as claimed in claim 7 wherein said mineral is crystal, quartz, feldspar, granite, periodotite, or glass.

9. A bioactivating composition as claimed in claim 1 wherein the silicon components are obtained by elution from an absorbent used for extraction of silicon components from the activated tissue.

10. A bioactivating composition as claimed in claim 1 wherein said silicon component content is more than 22 µg calculated as silicon per mg of dried composition.

11. A bioactivating composition as claimed in claim 1 wherein said silicon component content is more than 25 µg calculated as silicon per mg of dried composition.

12. A bioactivating composition as claimed in claim 2 wherein said silicon component content is more than 22 µg calculated as silicon per mg of dried composition.

13. A bioactivating composition as claimed in claim 3 wherein said silicon component content is more than 22 μg calculated as silicon per mg of dried composition.

14. A bioactivating composition as claimed in claim 1 wherein at least one silicon component is admixed with said extract from the activated tissue and the ratio of the silicon component content of said extract, calculated as silicon, to the total silicon component content of the bioactivating composition, calculated as silicon, is 1:3 to 1:10.

15. A bioactivating composition as claimed in claim 14 wherein said at least one silicon component which is admixed with said extract is selected from the group consisting of water-soluble silicic acids, water-soluble silicates, polymers of water-soluble silicic acids, polymers of water-soluble silicates, and mixtures thereof.

16. A method for making a bioactivating composition which suppresses histamine liberation and inhibits hyaluronidase activity comprising admixing an effective amount of an extract obtained from activated animal tissue infected with a poxvirus, said extract comprising at least one silicon component, with at least one additional silicon component to obtain a mixture, and drying the mixture to obtain a powder, wherein said powder exhibits positive color reactions to amino acid (by a ninhydrin reaction), saccharide (by an orcinol-iron (III) chloride-hydrochloric acid method), phosphorus (by a molybdenum blue method) and silicic acid (by a molybdenum blue method), and negative qualitative reactions to protein (by a trichloroacetic acid method), and phenol (by a ferric chloride method), and said powder has a silicon component content which is more than 20 μg calculated as silicon per mg of dried powder.

17. A method as claimed in claim 16 wherein said silicon component content is more than 22 μg calculated as silicon per mg of dried powder.

18. A method as claimed in claim 17 wherein the ratio of the silicon component content of said extract calculated as silicon to the total silicon component content of the powder calculated as silicon is 1:3 to 1:10.

19. A method as claimed in claim 16 wherein said at least one additional silicon component which is admixed with said extract is selected from the group consisting of water-soluble silicic acids, water-soluble silicates, polymers of water-soluble silicic acids, polymers of water-soluble silicates, or mixtures thereof.

20. A method as claimed in claim 16 wherein said at least one additional silicon component comprises a silicic acid solution or sodium metasilicate, the at least one additional silicon component and said extract are admixed in water to obtain a mixture, and the mixture is evaporated to dryness to obtain said powder.

* * * * *